United States Patent [19]

Zajacek et al.

[11] Patent Number: 5,214,168

[45] Date of Patent: May 25, 1993

[54] INTEGRATED PROCESS FOR EPOXIDE PRODUCTION

[75] Inventors: John G. Zajacek, Devon, Pa.; Guy L. Crocco, Wilmington, Del.

[73] Assignee: Arco Chemical Technology, L.P., Wilmington, Del.

[21] Appl. No.: 876,884

[22] Filed: Apr. 30, 1992

[51] Int. Cl.$^5$ ............ C07D 301/12; C07D 303/04; C07D 303/08; C07D 303/14

[52] U.S. Cl. .................... 549/531; 423/591; 568/320; 568/814

[58] Field of Search ........................ 549/531

[56] References Cited

U.S. PATENT DOCUMENTS

| | | | |
|---|---|---|---|
| 2,125,412 | 8/1938 | Arnold et al. | 260/154 |
| 2,137,407 | 11/1938 | Lazier | 260/633 |
| 2,334,100 | 11/1943 | Ipatieff et al. | 260/668 |
| 2,400,959 | 5/1946 | Marvin | 260/690 |
| 2,544,756 | 3/1951 | Guest et al. | 252/470 |
| 2,544,771 | 3/1951 | Young et al. | 252/467 |
| 2,575,403 | 11/1951 | Young et al. | 260/618 |
| 2,575,404 | 11/1951 | Guest et al. | 260/618 |
| 2,869,989 | 1/1959 | Keeler et al. | 23/207 |
| 3,156,531 | 11/1964 | Luten et al. | 23/207 |
| 3,294,488 | 12/1966 | Dunlop et al. | 23/207 |
| 3,927,120 | 12/1975 | Grane et al. | 260/618 H |
| 3,927,121 | 12/1975 | Grane et al. | 260/618 H |
| 4,208,539 | 6/1980 | Rashkin | 568/814 |
| 4,303,632 | 12/1981 | Gosser | 423/591 |
| 4,396,783 | 8/1983 | Esposito et al. | 568/706 |
| 4,410,501 | 10/1983 | Taramasso et al. | 423/326 |
| 4,476,327 | 10/1984 | Neri et al. | 568/678 |
| 4,480,135 | 10/1984 | Esposito et al. | 568/385 |
| 4,656,016 | 4/1987 | Taramasso et al. | 423/277 |
| 4,666,692 | 5/1987 | Taramasso et al. | 423/326 |
| 4,701,428 | 10/1987 | Bellussi et al. | 502/8 |
| 4,824,976 | 4/1989 | Clerici et al. | 549/531 |
| 4,833,260 | 5/1989 | Neri et al. | 549/531 |
| 4,859,785 | 8/1989 | Bellussi et al. | 549/531 |
| 4,897,252 | 1/1990 | Cochran et al. | 423/591 |
| 4,937,216 | 1/1990 | Clerici et al. | 502/62 |
| 4,975,266 | 12/1990 | Albal et al. | 423/591 |
| 4,996,374 | 2/1991 | Lin et al. | 568/814 |
| 5,039,508 | 8/1991 | Cochran et al. | 423/591 |
| 5,082,641 | 1/1992 | Popa et al. | 423/326 |

FOREIGN PATENT DOCUMENTS

| | | |
|---|---|---|
| 1001038 | 6/1989 | Belgium . |
| 9262 | 4/1980 | European Pat. Off. ........ 549/531 |
| 0129814 | 1/1985 | European Pat. Off. . |
| 0132550 | 2/1985 | European Pat. Off. . |
| 0190609 | 3/1986 | European Pat. Off. . |
| 0265018 | 4/1988 | European Pat. Off. . |
| 0311983 | 4/1989 | European Pat. Off. . |
| 0315247 | 5/1989 | European Pat. Off. . |
| 0315248 | 5/1989 | European Pat. Off. . |
| 1505332 | 12/1967 | France . |
| 204147 | 9/1986 | Japan . |
| 758907 | 10/1956 | United Kingdom . |
| 1209321 | 10/1970 | United Kingdom ........ 549/531 |

OTHER PUBLICATIONS

Kirk-Othmer "Encyclopedia of Chem. Tech." vol. II 2nd ed. pp. 398–402.
Huybrechts et al., *J. Mol. Catal.* 71, 129 (1992).
Clerici et al., *J. Catal.* 129, 159 (1991).
Notari, in "Innovation in Zeolite Material Science," *Studies in Surface Science and Catalysts*, vol. 17, p. 413 (1988).
Kharasch et al., *J. Org. Chem.* 23, 1322 (1958).
Milas, et al., *J. Am. Chem. Soc.* 81, 6461 (1959).
Thangaraj et al., *J. Catal.* 130, 1 (1991).
Reddy et al., *Applied Catal.* 58, L-1 (1990).
Reddy et al., *J. Catal.*, 130, 440 (1991).
Reddy et al., *Zeolites* 12, 95 (1992).
Huybrechts et al., *Catal. Letter* 8, 237 (1991).
Bellussi et al., *J. Catal.*, 133, 220 (1992).
Szostak, *Molecular Sieves—Principles of Synthesis and Identification*, pp. 250–252 (1989).
Freifelder, *Practical Catalytic Hydrogenation* pp. 12–13 (1971).
Fieser et al., *Reagents for Organic Synthesis* p. 778 (1967).
Breitner et al., *J. Org. Chem.* 24, 1855 (1959).
Rylander et al., *Engelhard Ind., Inc., Tech. Bull*, 8(4), 148 (1968).

*Primary Examiner*—Joseph E. Evans
*Attorney, Agent, or Firm*—Stephen D. Harper

[57] ABSTRACT

Epoxides are produced by an integrated process involving air oxidation of an aryl-substituted secondary alcohol, epoxidation of an olefin by the secondary alcohol oxidation product in the presence of a titanium silicalite catalyst, and generation of the secondary alcohol by hydrogenation.

28 Claims, 1 Drawing Sheet

INTEGRATED PROCESS FOR EPOXIDE PRODUCTION

FIELD OF THE INVENTION

This invention relates to an integrated process for producing an epoxide wherein the only reactants consumed in the overall process are olefin, molecular oxygen, and hydrogen. In particular, the invention pertains to a process whereby an oxidant mixture comprised of an aryl-substituted secondary alcohol, an aryl-substituted ketone, and hydrogen peroxide is generated by reaction of the alcohol with molecular oxygen and then reacted with an ethylenically unsaturated substrate in the presence of a titanium silicalite catalyst. The aryl-substituted ketone is recycled back to alcohol by hydrogenation.

BACKGROUND OF THE INVENTION

Epoxides such as ethylene oxide, propylene oxide, 1,2-butene oxide and the like are useful intermediates for the preparation of a wide variety of products. The oxirane functionality in such compounds is highly reactive and may be ring-opened with any number of nucleophilic reactants. For example, epoxides may be hydrolyzed to yield glycols useful as anti-freeze components or reactive monomers for the preparation of condensation polymers such as polyesters.

Polyether polyols generated by the ring-opening polymerization of epoxides are widely utilized as intermediates in the preparation of polyurethane foams, elastomers, sealants, coatings, and the like. The reaction of epoxides with alcohols provides glycol ethers, which may be used as polar solvents in a number of applications.

Many different methods for the preparation of epoxides have been developed. One such method involves the use of certain titanium silicalite compounds to catalyze olefin oxidation by hydrogen peroxide. This method is described, for example, in Huybrechts et al., *J. Mol. Catal.* 71, 129(1992), U.S. Pat. Nos. 4,824,976 (Clerici et al.) and 4,833,260 (Neri et al.), European Pat. Pub. Nos. 311,983, 190,609, 315,247 and 315,248, Belgian Pat. Pub. No. 1,001,038, Clerici et al., *J. Catal.* 129,159(1991), and Notari, in "Innovation in Zeolite Material Science," *Studies in Surface Science and Catalysts*, Vol. 37, p. 413 (1988).

However, the outcome of synthetic reactions catalyzed by titanium silicalites is highly unpredictable and seemingly minor changes in reactants and conditions may drastically change the type of product thereby obtained. For example, when an olefin is reacted with hydrogen peroxide in the presence of titanium silicalite the product obtained may be either epoxide (U.S. Pat. No. 4,833,260), glycol ether (U.S. Pat. No. 4,476,327), or glycol (Example 10 of U.S. Pat. No. 4,410,501).

The prior art related to titanium silicalite-catalyzed epoxidation teaches that it is beneficial to employ a hydrogen peroxide solution that does not contain large amounts of water and recommends the use of an organic solvent as a liquid medium for the epoxidation reaction. Suitable solvents are said to include polar compounds such as alcohols, ketones, ethers, glycols, and acids. Solutions in tert-butanol, methanol, acetone, acetic acid, and propionic acid are taught to be most preferred. However, hydrogen peroxide is currently available commercially only in the form of aqueous solutions. To employ one of the organic solvents recommended by the prior art, it will thus be necessary to exchange the water of a typical hydrogen peroxide solution for the organic solvent. This will necessarily increase greatly the overall costs associated with an epoxidation process of this type. Additionally, concentration of hydrogen peroxide to a pure or nearly pure state is exceedingly dangerous and is normally avoided. Thus, it will not be practicable or cost-effective to simply remove the water by distillation and replace it with the organic solvent. Since hydrogen peroxide has a high solubility in and high affinity for water, liquid-liquid extraction of hydrogen peroxide from an aqueous phase to an organic phase will not be feasible. Moreover, many of the solvents taught by the prior art to be preferred for epoxidation reactions of this type such as tert-butanol, acetone, and methanol are water miscible and thus could not be used in such an extraction scheme. An epoxidation process wherein a readily obtained oxidant solution containing hydrogen peroxide and an organic solvent which promotes high yields of epoxide products is employed would thus be of significant economic advantage.

SUMMARY OF THE INVENTION

This invention provides an integrated process for the production of an epoxide comprising the steps of (a) contacting an aryl-substituted secondary alcohol with molecular oxygen under conditions effective to form an oxidant mixture comprised of the secondary alcohol, an aryl-substituted ketone corresponding to said secondary alcohol, and hydrogen peroxide;

(b) contacting the oxidant mixture with an olefin and a catalytically effective amount of a titanium silicalite for a time and at a temperature effective to convert the olefin to epoxide; and (c) reacting the aryl-substituted ketone with hydrogen in the presence of a transition metal hydrogenation catalyst under conditions effective to convert the ketone to the aryl-substituted secondary alcohol.

DETAILED DESCRIPTION OF THE INVENTION

Figure 1:
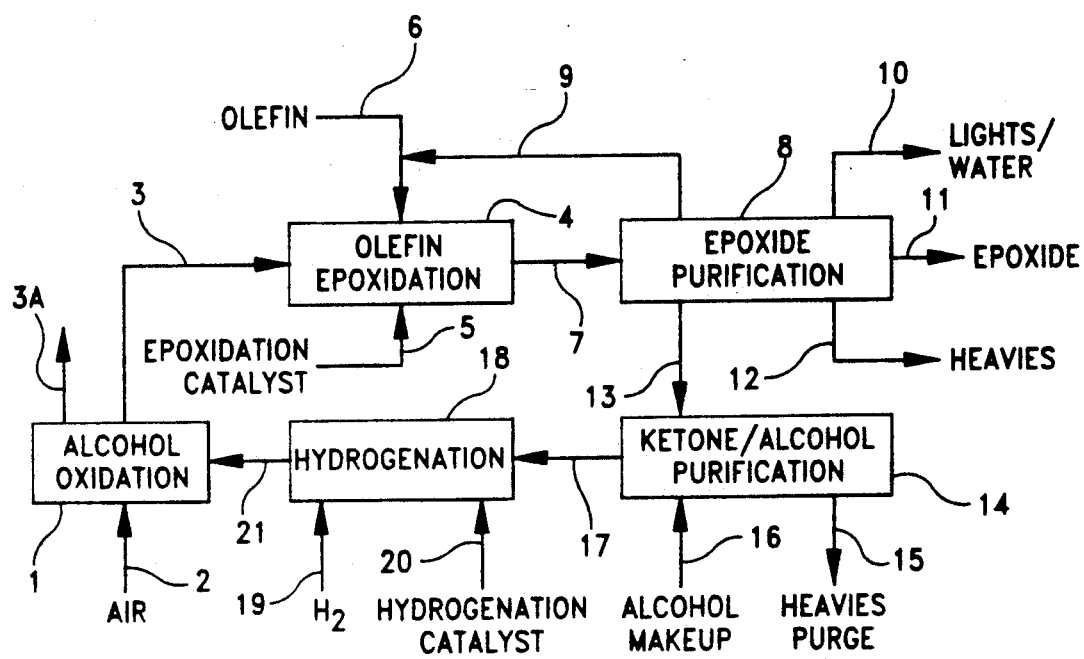
FIG. 1 illustrates in schematic form a suitable embodiment of the process of the invention.

It has now been surprisingly discovered that exceptionally high yields of epoxide are conveniently and economically realized through the utilization of an integrated process wherein a crude oxidant mixture generated by air oxidation of an aryl-substituted secondary alcohol is contacted with olefin in the presence of a titanium silicalite catalyst. The aryl-substituted ketone co-product is readily converted in whole or in part by hydrogenation back to alcohol for a further air oxidation/epoxidation cycle. The titanium silicalite catalyst shows little tendency to be deactivated or poisoned by the contaminants in the crude oxidant mixture, rendering the process highly suitable for use on a commercial scale.

The high epoxide selectivities achieved with the process of this invention were unexpected in view of the fact that the oxidant mixture, which contains a number of different chemical substances, may be employed directly in the epoxidation step without a tedious or costly preliminary purification. For example, minimal glycol ether and glycol by-products are formed even though substantial amounts of both water and alcohol, which are known to react readily with epoxide in the presence of titanium silicalite, are typically present in the oxidant mixture.

Another surprising aspect of the process of the invention is that high selectivity to epoxide is attained in spite of the fact that substantial amounts of aryl-substituted secondary alcohol are present during epoxidation. The prior art teaches that primary and secondary alcohols such as benzyl alcohol are readily oxidized to the corresponding aldehydes and ketones by reacting with hydrogen peroxide in the presence of titanium silicalite (U.S. Pat. No. 4,480,135). It has now been discovered that only minimal oxidation of an aryl-substituted secondary alcohol to an aryl-substituted ketone takes place during epoxidation, despite the fact that both olefin and alcohol are known to react with hydrogen peroxide in the presence of titanium silicalite and thus would be expected to compete for the available active oxygen. The finding that nearly all of the hydrogen peroxide reacts selectively with the olefin substrate and not with the secondary alcohol was thus quite unexpected.

The overall process of this invention may thus be represented as follows:

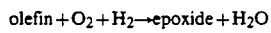

olefin + $O_2$ + $H_2$ → epoxide + $H_2O$ wherein the epoxide is the only organic species produced (other than minor quantities of by-products) and the olefin is the only organic species consumed. The process is consequently exceedingly attractive from a commercial point of view.

In the molecular oxygen oxidation step of the process, the selection of an aryl-substituted secondary alcohol is critical to the attainment of the highest possible epoxide yields, as oxidant mixtures obtained by oxidation of other types of alcohols have been found to provide unsatisfactorily low rates of epoxidation and/or low epoxide selectivity. Without wishing to be bound by theory, it is believed that the superior results achieved using aryl-substituted secondary alcohol are attributable to the propensity of dialkyl-substituted alcohols to yield oxidant mixtures upon air oxidation wherein relatively high proportions of active oxygen-containing organic compounds (peroxides and hydroperoxides) rather than free hydrogen peroxide are present.

For example, air oxidation of cyclohexanol is reported to yield cyclohexanone peroxide (also referred to as cyclohexanol hydroperoxide) rather than a mixture of cyclohexanone and free hydrogen peroxide (European Pat. Pub. 129,814). Cyclohexanone and hydrogen peroxide are known to react to form 1,1'-dihydroxy dicyclohexyl peroxide (Kharasch et al., J. Org. Chem. 23, 1322 (1958). Similarly, air oxidation of isopropanol produces a crude oxidant mixture containing substantial amounts of organic peroxides in addition to hydrogen peroxide (see J. Am. Chem. Soc. 81, 6461 (1959); U.S. Pat. Nos.,2,869,989, 3,156,531, and 3,294,488; British Pat. No. 758,907).

The secondary alcohols suitable for use include those organic compounds containing at least one carbon atom bearing a hydrogen, a hydroxyl group, and at least one aryl group such as those substances corresponding to the general structure

wherein R and $R^1$ are the same or different and are selected from the group consisting of alkyl, aryl alkyl (i.e., an aryl substituted alkyl group , and aryl groups provided that at least one of R or $R^1$ is an aryl group.

Preferred alkyl groups include $C_1$–$C_6$ alkyl groups such as methyl, ethyl, propyl, n-butyl, isobutyl, sec-butyl, tert-butyl, n-pentyl, isopentyl, 1-methylbutyl, 1-ethyl propyl, neopentyl, tert-pentyl, cyclopentyl, n-hexyl, isohexyl, cyclohexyl, and the like. If an alkyl group is present, it preferably does not contain any secondary or tertiary carbons (carbons bearing only one or two hydrogen atoms). Preferred aryl groups include $C_6$–$C_{18}$ aryl groups such as phenyl, mathylphenyl, dimethylphenyl, trimethylphenyl, nitrophenyl, chlorophenyl, bromophenyl, cyanophenyl, methoxyphenyl, anthryl, phenanthryl, biphenyl, and the like. Preferred aryl alkyl groups include $C_7$–$C_{20}$ aryl alkyl groups such an benzyl and phenethyl. The substituents on R and $R^1$, if any, should be selected so as not to interfere with the desired air oxidation, epoxidation, and hydrogenation reactions. The R and $R^1$ groups may be connected so as to form a cyclic structure, as in 9-hydroxyfluorene. More than one hydroxyl group may be present. If an alkyl group is present, it is preferably a methyl group. Unsubstituted aryl groups are preferred for use in view of their relative inertness under the reaction conditions of the process. Most preferably, R is methyl and $R^1$ is phenyl (i.e., the aryl-substituted secondary alcohol is alpha-methyl benzyl alcohol, which is also known as phenethyl alcohol and methyl phenyl carbinol). Examples of other useful alcohols include benzhydrol (R and $R^1$ are both phenyl), alpha-ethylbenzyl alcohol (R is ethyl, $R^1$ is phenyl), alpha-methyl naphthyl alcohol (R is methyl, $R^1$ is naphthyl), and the like.

Also suitable for use as the aryl-substituted secondary alcohol component of the invention is the class of anthraquinols (also referred to anthrahydroquinones) corresponding to the general structure

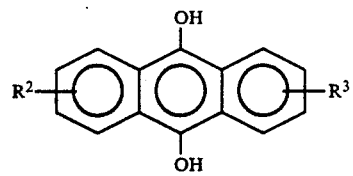

wherein $R^2$ and $R^3$ are the same or different and are selected from hydrogen and $C_1$–$C_{10}$ alkyl. Illustrative examples of this class of aryl-substituted secondary alcohols include 2-ethylanthroquinol, 2-tert-butyl anthraquinol, 2-tert-amyl anthraquinol.

The secondary alcohol is preferably selected such that it is a liquid at the reaction temperatures employed during each step of the process and is miscible with or is capable of dissolving the other components of the reaction mixture other than the titanium silicalite and hydrogenation catalysts (that is, it acts as a solvent). It is desirable that the secondary alcohol have a boiling point at atmospheric pressure of from about 175° C. to 350° C. If the secondary alcohol is a solid at the reaction temperature used during any step of the process, it will generally be desirable to employ a solvent so as to maintain the reaction components as a liquid phase.

The aryl-substituted secondary alcohol is reacted with molecular oxygen from a suitable source such as air to yield the oxidant mixture, which will typically contain excess aryl-substituted secondary alcohol, the aryl-substituted ketone resulting from reduction of the secondary alcohol (and which will have the same hydrocarbon skeleton as the alcohol), hydrogen peroxide, and water. The starting material to be air-oxidized may contain minor amounts of the aryl-substituted ketone in addition to the alcohol. Generally speaking, the oxidation conditions are adjusted so as to yield an oxidant mixture comprised of at least 30 weight percent aryl-substituted secondary alcohol, from about 1 to 10 weight percent hydrogen peroxide and less than 4 weight percent water (the balance being predominantly aryl-substituted ketone). The oxidation may be either uncatalyzed or catalyzed (for example, by introduction of a minor amount of a peroxide or hydroperoxide such as t-butyl hydroperoxide), but is most preferably carried out under the conditions described in U.S. Pat. Nos. 4,897,252, 4,975,266, and 5,039,508 (the teachings of these patents are incorporated herein by reference in their entirety). Temperatures of from 100° to 200° C. (more preferably, from 120° to 180° C.) will typically be appropriate for use in order to attain reasonable oxidation rates. The preferred range of oxygen partial pressure in the feed gases (which may include an inert diluent gas such as nitrogen in addition to oxygen) is 5 to 500 psia (more preferably, 15 to 250 psia) partial pressure. Total pressure in the oxidation reaction zone should be sufficient to maintain the components of the reaction mixture in the liquid phase (50 psia to 1000 psia is normally sufficient).

In the epoxidation step of the process of this invention, the oxidant mixture is contacted with an olefin and a catalytically effective amount of a titanium silicalite for a time and at at a temperature effective to convert the olefin to the desired epoxide.

The olefin substrate epoxidized in the process of this invention may be any organic compound having at least one ethylenically unsaturated functional group (i.e., a carbon-carbon double bond) and may be an aromatic, aliphatic, mixed aromatic-aliphatic (e.g., aralkyl), cyclic, branched or straight chain olefin. Preferably, the olefin contains from 2 to 30 carbon atoms (i.e., a $C_2-C_{30}$ olefin). More than one carbon-carbon double bond may be present in the olefin; dienes, trienes, and other polyunsaturated substrates thus may be used. Other examples of suitable substrates include unsaturated fatty acids or fatty acid derivatives such as esters or glycerides and oligomeric or polymeric unsaturated compounds such as polybutadiene.

The olefin may contain substituents other than hydrocarbon substituents such as halide, carboxylic acid, ether, hydroxyl, thiol, nitro, cyano, ketone, acyl, ester, anhydride, amino, and the like.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters), and alkenyl aromatic compounds such as styrene, alpha-methyl styrene, beta-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, archlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like.

Mixtures of olefins may be epoxidized and the resulting mixture of epoxides either employed in mixed form or separated into the different component epoxides.

The process of this invention is especially useful for the epoxidation of $C_2-C_{30}$ olefins having the general structure

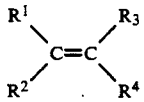

wherein $R^1$, $R^2$, $R^3$, and $R^4$ are the same or different and are selected from the group consisting of hydrogen, $C_1-C_{20}$ alkyl, $C_5-C_{12}$ cycloalkyl, $C_6-C_{20}$ alkyl cycloalkyl, $C_6-C_{20}$ aryl, and $C_7-C_{20}$ aryl alkyl.

The amount of hydrogen peroxide relative to the amount of olefin is not critical, but most suitably the molar ratio of hydrogen peroxide olefin is from about 100:1 to 1:100 when the olefin ontains one ethylenically unsaturated group. The molar ratio of ethylenically unsaturated groups in the olefin substrate to hydrogen peroxide is more preferably in the range of from 1:10 to 10:1. One equivalent of hydrogen peroxide is theoretically required to oxidize one equivalent of a monounsaturated olefin substrate, but it may be desirable to employ an excess of one reactant to optimize selectivity to the epoxide. A key advantage of the process of this invention as compared to other epoxidation processes is that neither a large molar excess of hydrogen peroxide relative to olefin or a large molar excess of olefin relative to hydrogen peroxide is required. High yields of epoxide may be realized using a slight (i.e., 5–75%) molar excess of olefin relative to hydrogen peroxide (i.e., the molar ratio of olefin to hydrogen peroxide is from 1.05:1 to 1.75:1). The hydrogen peroxide is thus used in a very efficient manner; little of the hydrogen peroxide is wasted through non-selective decomposition to water (i.e., without oxidation of an olefin molecule). Since hydrogen peroxide is relatively costly to generate, this means that the overall integrated process of the invention may be economically practiced on a commercial scale. Additionally, processing costs arising from recovery and recycling of olefin are minimized since there is no need to employ a large excess of olefin in order to optimize epoxide selectivity, in contrast to known epoxidation processes employing organic hydroperoxides and molybdenum-containing catalysts.

The titanium silicalites useful as catalysts in the epoxidation step of the process comprise the class of zeolitic substances wherein titanium is substituted for a portion of the silicon atoms in the lattice framework of a silicalite molecular sieve. Such substances are well-known in the art and are described, for example, in U.S. Pat. No. 4,410,501 (Taramasso et al.), U.S. Pat. No. 4,824,976 (Clerici et al.), U.S. Pat. No. 4,666,692 (Taramasso et al.), Thangaraj et al., *J. Catal.* 130, 1 (1991), Reddy et al., *Applied Catal.* 58, L-1 (1990), Reddy et al., *J. Catal.* 130, 440 (1991), Reddy et al., *Zeolites* 12, 95 (1992), Belgian Pat. Pub. No. 1,001,038 (Bellussi et al.), Huybrechts et al., *J. Mol. Catal.* 71, 129 (1992), Huybrechts et al., *Catal. Letter* 8, 237 (1991), U.S. Pat. No. 4,656,016 (Taramasso et al.), U.S. Pat. No. 4,859,785 (Bellussi et al.), European Pat. Pub. No. 265,018 (Bellussi et al.), U.S. Pat. No. 4,701,428 (Bellussi et al.), U.S. Pat. No. 4,937,216 (Clerici et al.), European Pat. Pub. No. 311,983 (Padovan et al.), European Pat. Pub. No. 132,550 (Saleh), U.S. Pat. No. 5,082,641 (Popa et al.), Clerici et al., *J. Catal.* 129,159 (1991), Bellussi et al., *J. Catal.* 133, 220 (1992), Szostak, *Molecular Sieves-Principles of Synthesis and Identification*, pp. 250–252 (1989), and Notari, "Synthesis and Catalytic Properties of Titanium Containing Zeolites", *Innovation in Zeolite Materials Science*, Grobet et al., Eds., 413 (1988). The teachings of these publications are incorporated herein by reference in their entirety.

Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). The titanium silicalite preferably contains no metals other than titanium and silica in the lattice framework.

Preferably, essentially all of the titanium present is in the zeolite-like lattice framework. The catalyst itself preferably does not contain any appreciable amount of any amorphous phase or a crystalline phase other than the crystalline titanium silicalite phase. As will be explained subsequently, however, the use of a binder or support in combination with the titanium silicalite may be advantageous under certain circumstances.

Catalysts suitable for use in the process of this invention will have a composition corresponding to the following empirical formula $xTiO_2 \cdot (1-x)SiO_2$, where x is between 0.0001 and 0.500. More preferably, the value of x is from 0.01 to 0.125. The molar ratio of Si:Ti in the lattice framework of the titanium silicalite is advantageously from 9.5:1 to 99:1 (most preferably, from 9.5:1 to 60:1). The use of titanium-rich silicalites as described in co-pending U.S. application Ser. No. 07/876,882, Apr. 30, 1992, entitled "Epoxidation PRocess Using Titanium-Rich Silicalite Catalysts" is particularly preferred wherein x is between 0.045 and 0.125.

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of organic solvent as well as catalyst activity. Typically, however, the amount of catalyst will be from 0.01 to 10 grams per mole of olefin. The concentration of titanium in the total epoxidation reaction mixture will generally be from about 10 to 10,000 ppm.

The catalyst may be utilized in powder, pellet, microspheric, monolithic or any other suitable physical form. The use of a binder (co-gel) or support in combination with the titanium silicalite may be advantageous. Supported or bound catalysts may be prepared by the methods known in the art to be effective for zeolite catalysts in general.

Illustrative binders and supports include silica, alumina, silica-alumina, silica-titania, silica-thoria, silica-magnesia, silica-zironia, silica-beryllia, and ternary compositions of silica with other refractory oxides. Also useful are clays such as montmorillonites, koalins, bentonites, halloysites, dickites, nacrites, and ananxites. The proportion of titanium silicalite:binder or support may range from 99:1 to 1:99, but preferably is from 5:95 to 80:20. The methods described in U.S. Pat. No. 4,701,428 (incorporated herein by reference in its entirety) may be adapted for the preparation of microspheres containing oligomeric silica binder and titanium silicalite crystals which are suitable and preferred for use in the process of this invention.

The catalyst may be treated with an alkaline (basic) substance or a silylating agent so as to reduce the surface acidity, as described in U.S. Pat. No. 4,937,216.

While the aryl-substituted secondary alcohol and aryl-substituted ketone present in the oxidant mixture serve as an effective reaction medium for the epoxidation step, it may be advantageous to employ an additional co-solvent such as a ketone (e.g., acetone, methyl ethyl ketone), alcohol (e.g., methanol, ethanol, isopropanol, n-butanol, t-butanol), ether (e.g., diethyl ether, tetrahydrofuran, dioxane), nitrile (e.g., acetonitrile), aliphatics or aromatic hydrocarbon, halogenated hydrocarbon, and the like. The use of methanol as a co-solvent is particularly preferred, as even relatively low concentrations of this co-solvent (5–40 weight percent of the total reaction mixture) have been found to markedly improve the rate of reaction and epoxide selectivity.

The reaction temperature is not critical, but should be sufficient to accomplish substantial conversion of the olefin to epoxide within a reasonably short period of time. It is generally advantageous to carry out the reaction to achieve as high a hydrogen peroxide conversion as possible, preferably at least 50% and desirably at least 90%, consistent with reasonable selectivities. The optimum reaction temperature will be influenced by catalyst activity, olefin reactivity, reactant concentrations, and type of solvent employed, among other factors, but typically will be in a range of from about 0° C. to 150° C. Reaction times of from about 10 minutes to 48 hours will typically be appropriate, depending upon the above-identified variables. Although sub-atmospheric pressures can be employed, the reaction is preferably performed at atmospheric pressure or at elevated pressure (typically, between 1 and 100 atmospheres). Generally, it will be desirable to maintain the reaction components as a liquid mixture.

The epoxidation step of this invention may be carried out in a batch, continuous, or semi-continuous manner using any appropriate type of reaction vessel or apparatus such as a fixed bed, transport bed, stirred slurry, or CSTR reactor. Known methods for conducting metal-catalyzed epoxidations of olefins using hydrogen peroxide will generally also be suitable for use. Thus, the reactants may be combined all at once or sequentially. For example, the hydrogen peroxide may be added incrementally to the reaction zone.

Once the epoxidation has been carried out to the desired degree of conversion, the epoxide product may be separated and recovered from the reaction mixture using any appropriate technique such as fractional distillation extractive distillation, liquid-liquid extraction, crystallization, or the like. After separating from the epoxidation reaction mixture by any suitable method such as filtration, the recovered titanium silicalite catalyst may be economically re-used in subsequent epoxidations. Similarly, any unreacted olefin or hydrogen peroxide may be separated and recycled or otherwise disposed of.

The epoxide and unreacted olefin are preferably separated from the aryl-substituted secondary alcohol and aryl-substituted ketone prior to the hydrogenation step of the process. However, if desired, the epoxide and olefin may be converted to alcohol and saturated hydrocarbon respectively by subjecting these components to hydrogenation. In the hydrogenation step, the aryl-substituted ketone is reacted with hydrogen in the presence of a transition metal hydrogenation catalyst under conditions effective to convert all or a portion of the ketone to the aryl-substituted secondary alcohol. The transition metal in the hydrogenation catalyst is most preferably palladium, platinum, rhodium, chromium (as in copper chromite), rhodium, nickel, or ruthenium. The hydrogenation is suitably carried out at a temperature of from 0° C. to 200° C. and a hydrogen pressure of between 1 and 200 atmospheres.

Transition metal-containing catalysts suitable for use in the hydrogenation step of the process of this invention include, but are not limited to, palladium supported on a carrier such as activated carbon (charcoal), silica gel, alumina, alkaline earth carbonate, or sulfate, diatomaceous earth, pumice and the like (especially supported palladium catalysts which have been pretreated with a basic compound such as aqueous sodium hydroxide, as described in Japanese Kokai Pat. Pub. No. 61-204147), catalysts comprising copper distributed in a zinc oxide matrix (such catalysts, which may also be referred to as reduced copper oxide-zinc oxide catalysts, are described in U.S. Pat. Nos. 3,927,120 and 4,927,121), copper chromite catalysts (as described in U.S. Pat. Nos. 2,137,407 and 2,125,412) barium-copper chromite catalysts containing zinc (as described in U.S. Pat. No. 4,208,539), Raney nickel, palladium oxide, palladium black, ruthenium supported on carbon or alumina, nickel supported on diatomaceous earth, platinum supported on carbon, rhodium supported on carbon, ruthenium supported on carbon, rhodium-platinum oxide catalysts, copper-chromium catalysts (as described in U.S. Pat. Nos. 2,544,756, 2,544,771, 2,575,403, and 2,575,404), catalysts comprising calcium oxide, copper oxide, and vanadium oxide (as described in U.S. Pat. No. 2,400,959), and catalysts containing copper, zinc, and alumina obtained by hydrogenative reduction of a precursor pellets comprising an aluminum oxide matrix, zinc oxide, and cupric oxide (as described in U.S. Pat. No. 2,334,100). The temperature, hydrogen pressure, and catalyst concentration during hydrogenation are selected so as to accomplish substantial (i.e., at least 50% and more preferably at least 80%) conversion of the aryl-substituted ketone to aryl-substituted secondary alcohol within a practicably short reaction time (i.e., approximately 15 minutes to 12 hours) without overreduction of the ketone to aliphatic or aromatic compounds which do not contain hydroxyl groups. The optimum hydrogenation conditions will vary depending upon the type of catalyst selected for use and the reactivity of the aryl-substituted ketone, but may be readily determined by one skilled in the art with minimal experimentation based on the known art pertaining to ketone hydrogenation. Typically, temperatures of from about 20° C. to 175° C. and hydrogen pressures of from about 1 to 200 atmospheres will be appropriate for use. Catalyst concentrations of from about 0.1 to 10 weight percent based on the weight of the ketone/alcohol mixture recovered after removal of epoxide will generally be suitable.

In a particularly preferred embodiment of this invention, the transition metal hydrogenation catalyst is palladium supported on carbon, alumina, or other suitable support. Such catalysts are well-known and are described, for example, in Friefelder, *Practical Catalytic Hydrogenation*, pp. 12-13 (1971) and Fieser, et al., *Reagents for Organic Synthesis*, p. 778 (1967).

Numerous supported palladium catalysts are also available from commercial sources. The amount of palladium on the support or carrier is not critical, but typically will vary from about 1 to 20 weight percent. The catalyst will desirably have a relatively high surface area (i.e., at least about 400 m$^2$/g). Appropriate hydrogenation temperatures for use with such catalysts range from about 20° C. to 150° C., with temperatures of 30° C. to 100° C. being especially preferred. Hydrogen pressures of at least 5 psia are employed, although faster rates of hydrogenation are realized at hydrogen pressures of from 70 to 400 psia. The supported palladium catalyst is preferably treated with a solution of alkali metal or alkaline earth hydroxide, carbonate, oxide, carboxylate or other basic substance. It may be advantageous for the ketone/alcohol mixture to contain a minor amount of water (e.g., from 1 to 5 weight percent) in order to minimize catalyst deactivation upon prolonged operation.

The hydrogenation step may be carried out in a batch, semi-batch, continuous, or semi-continuous manner using any suitable reaction vessel or apparatus wherein the ketone may be intimately contacted with the transition metal hydrogenation catalyst and hydrogen. As the catalyst is normally heterogeneous in nature, fixed bed or slurry-type reactors are especially convenient for use.

FIG. 1 illustrates one embodiment of the integrated epoxidation process of this invention wherein a relatively light olefin such as propylene is epoxidized to yield a volatile epoxide. A stream comprised of aryl-substituted secondary alcohol passes via line 21 into alcohol oxidation zone 1 wherein the secondary alcohol is reacted with molecular oxygen to form an oxidant stream comprised of hydrogen peroxide, aryl-substituted ketone, and excess aryl-substituted secondary alcohol. The molecular oxygen is provided by air introduced via line 2. The temperature, pressure and the rates of addition and concentration of the reactants are preferably maintained in zone 1 effective to maintain the oxygen absorption rate in the liquid phase at 90% or more of the maximum oxygen absorption rate. The water content of the reaction mixture is desirably maintained below 4 wt. %, preferably below 2 wt. % and most preferably below 1 wt. % by stripping water formed during the oxidation out of the reaction mixture with unreacted oxygen and/or inert gases via line 3A. Preferably, the oxygen partial pressure in these gases is regulated at a value not more than 3.0, preferably not more than 2.0, times the minimum value at the maximum oxygen absorption rate.

In especially preferred practice, reaction zone 1 is comprised of a plurality of separate reaction zones. The liquid reaction mixture is passed in series from one zone to the next while the oxygen-containing gas it introduced in parallel to each of the reaction zones. Each zone is thoroughly back-mixed. Hydrogen peroxide concentration is lowest in the first zone and increases in each successive zone, reaching a maximum in the final zone.

The oxidant mixture containing hydrogen peroxide passes from zone 1 via line 3 and may be used directly as the source of oxidant in the olefin epoxidation reaction which takes place in olefin epoxidation zone 4. Alternatively, the oxidant stream may be further processed or purified prior to introduction into zone 4, although a distinct advantage of this process is that such a purification is not necessary in order to achieve high epoxide yields.

The olefin to be epoxidized is fed into zone 4 via line 6, while the titanium silicalite catalyst is introduced via line 5. Alternatively, the titanium silicalite may be deployed in zone 4 as a fixed bed. The resulting reaction mixture is maintained at the desired temperature and pressure in zone 4 for a time sufficient to convert at least a portion, and preferably at least about 50%, of the olefin to epoxide, thereby consuming a portion of the hydrogen peroxide (preferably, substantially all of the hydrogen peroxide is consumed). The crude epoxidation product thus obtained passes through line 7 to epoxide purification zone 8 where it is separated by fractional distillation or other such means into a recycled olefin stream (returned to olefin feed line 6 or olefin epoxidation zone 4 via line 9), a lights stream containing water and/or organics having a boiling point less than that of the epoxide (withdrawn via line 10), an epoxide stream containing the desired epoxide product (withdrawn via line 11), and an ketone/alcohol stream comprised of the secondary alcohol and the corresponding ketone (withdrawn via line 13). If unreacted hydrogen peroxide is present, it may either be removed in the form of an aqueous or organic solution or decomposed by some suitable method. If a co-solvent such as methanol has been used, it is preferably separated from the epoxidation reaction mixture by distillation or other similar means and recycled to zone 4. If desired, a heavies stream containing organic compounds having boiling points higher than that of the alcohol and ketone as well as the titanium silicalite catalyst may be separated and withdrawn via line 12. The titanium silicalite catalyst may be recovered from this stream and returned to the olefin epoxidation zone via line 5. Alternatively, the titanium silicalite may be recovered and recovered from the epoxidation reaction product prior to separation of any of the organic components thereof.

Optionally, further purification of the ketone/alcohol stream may be carried out in ketone/alcohol purification zone 14 by any suitable means such as distillation, countercurrent extraction, or the like. Certain compounds such as phenols may be present in the ketone/alcohol stream which may tend to inhibit the molecular oxygen oxidation of the secondary alcohol to hydrogen peroxide and ketone. It is therefore desirable to treat this stream in zone 14 to remove such compounds or to convert them into non-inhibitive compounds. Preferably, zone 14 comprises both distillation and caustic and/or ion exchange treatment means. Additionally heavies may be withdrawn via line 15 and make-up secondary alcohol introduced via line 16 as necessary. The purified ketone/alcohol stream is passed via line 17 to hydrogenation zone 18 wherein the stream is reacted with hydrogen (introduced via line 19) in the presence of a suitable hydrogenation catalyst such as a supported platinum, nickel, copper chromite, ruthenium, or palladium catalyst (introduced via line 20 or deployed as a fixed bed in zone 18) so as to convert at least a portion, and preferably substantially all, of the aryl-substituted ketone generated in alcohol oxidation zone 1 back to aryl-substituted secondary alcohol. The hydrogenated stream produced in zone 18 is passed via line 21 to alcohol oxidation zone 1. This integrated process is preferably operated in a continuous manner such that the desired epoxide is the only major organic product and the ketone is recycled.

From the foregoing description, one skilled in the art can readily ascertain the essential characteristics of this invention, and, without eparting from the spirit and scope thereof, can make various changes and modifications of the invention to adapt it to various usages, conditions, and embodiments.

The following examples further illustrate the process of this invention but are not limitative of the invention in any manner whatsoever.

EXAMPLE 1

Step A

An oxidant mixture was prepared by air oxidation of alpha-methyl benzyl alcohol in accordance with the procedures of U.S. Pat. No. 5,039,508, said mixture comprising ca. 5 weight % hydrogen peroxide 1 weight % water, 66 weight % alpha-methyl benzyl alcohol, and 28 weight % acetophenone. Minor amounts of active oxygen-containing organic compounds such as ethyl benzene dihydroperoxide and ethyl benzene hydroperoxide were also present.

Step B

The oxidant mixture generated in Step A (100 mL) was charged to an Isco pump. A 300 mL glass-lined autoclave was charged with "TS-1" titanium silicalite catalyst (0.56 g), methanol (25 mL), and propylene (16 mL; 0.20 mole) and heated to 40° C. The oxidant mixture in the Isco pump was added to the contents of the autoclave while stirring. The molar ratio of olefin to hydrogen peroxide was ca. 1.5:1. The reaction mixture was stirred for an additional 2 hours at 40°-50° C. after addition of the oxidant mixture was completed. Analysis of the reaction product indicated that 70% hydrogen peroxide conversion and 89% selectivity to to propylene oxide based on hydrogen peroxide had been achieved.

Step C

The components of the reaction epoxidation product are recovered by removing the insoluble titanium silicalite catalyst by filtration and distilling off the propylene oxide (b.p. 34° C./760 mm Hg). The bottoms fraction containing alpha-methyl benzyl alcohol is combined with a commercially available 5% palladium on activated carbon catalyst (5 parts by weight catalyst per 100 parts by weight of the bottoms fraction) and reacted 2 hours at 50° C. under a hydrogen atmosphere (200 psia) to achieve at least 80% conversion of the acetophenone to alpha-methyl benzyl alcohol. The hydrogenated product may subsequently be re-oxidized with molecular oxygen to yield a new oxidant mixture suitable for use in another olefin epoxidation cycle.

EXAMPLE 2

Example 1 was repeated using a larger amount (1.12 g) of titanium silicalite catalyst. The conversion of hydrogen peroxide in Step B was increased to 87% while the propylene oxide selectivity remained high (88%).

COMPARATIVE EXAMPLE 3

This example demonstrates the advantages of employing an oxidant mixture derived from an aryl-substituted secondary alcohol in the integrated process of this invention instead of an oxidant mixture derived from cyclohexanol.

An oxidant mixture nominally comprised of cyclohexanol (65 weight %), cyclohexanone (30 weight %), and hydrogen peroxide (5 weight %; 0.15 mole) was contacted with propylene (16 mL; 0.20 mole) in the presence of "TS-1" titanium silicalite (containing 1.4 weight % Ti) for 45 minutes at 80° C. The oxidant mixture had been prepared by stirring a mixture of cyclohexanol (70 mL), cyclohexanone (30 mL), 50% aqueous hydrogen peroxide (10 mL) for 4 hours at room temperature, adding magnesium sulfate (30 g), stirring for an additional 30 minutes, and then filtering (the resulting oxidant mixture closely approximated the reaction product obtained by air oxidation of cyclohexanol and contained a high proportion of a dimeric organic peroxide species resulting from combination of the cyclohexanone and hydrogen peroxide). Hydrogen peroxide conversion was only 32%. Hydrogen peroxide conversion was only 32%. Selectivity to propylene oxide was relatively low (53% based on hydrogen peroxide), resulting in an overall yield of epoxide of only 17% as compared to yields of about 81% using an oxidant mixture derived from alpha-methyl benzyl alcohol under comparable conditions.

COMPARATIVE EXAMPLE 4

This example demonstrates the advantages of utilizing an oxidant mixture derived from an aryl-substituted secondary alcohol in the integrated process of the invention instead of an oxidant mixture derived from isopropanol.

An oxidant mixture nominally comprised of isopropanol (ca. 66 weight %), acetone ca. 29 weight %), and hydrogen peroxide (5 weight %; 0.15 mole) was contacted with propylene (16 mL; 0.20 mole) in the presence of "TS-1" titanium silicalite (1.4 weight % Ti) for 4 hours at 80° C. The oxidant mixture had been prepared by stirring a mixture of isopropanol (70 mL), acetone (30 mL), and 50% aqueous hydrogen peroxide (10 mL) at room temperature for 4 hours, adding magnesium sulfate (30 g), stirring for an additional 30 minutes before filtering to remove the magnesium sulfate (the resulting oxidant mixture closely approximated the reaction product obtained by air oxidation of isopropanol and contained a high proportion of a dihydroperoxy compound resulting from combination of acetone and hydrogen peroxide). While the conversion of active oxygen species was comparable to that observed when using an alpha-methyl benzyl alcohol-derived oxidant mixture under similar conditions (94%), the selectivity to propylene oxide was only 70%. This was significantly lower than the ca. 83% selectivity obtained using alpha-methyl benzyl alcohol instead of isopropanol. At least part of the lower selectivity was due to the oxidation of isopropanol to acetone during the attempted epoxidation.

EXAMPLE 5

A titanium-rich silicalite catalyst containing an MFI crystalline phase and 4.4 weight percent titanium was prepared in accordance with the procedure described in Thangaraj et al., *J. Catal.*, 130,1(1991). The catalyst (0.73 g) was then charged to a 300 mL glass-lined autoclave together with methanol (25 mL) and then propylene (16 mL; 0.20 mole). The autoclave was equipped with a "Teflon" stir shaft and blade and a "Teflon" tape-wrapped thermowell. After heating the autoclave to 75° C. using an external heating coil, a oxidant mixture containing alpha-methyl benzyl alcohol, acetophenone, 5.15% hydrogen peroxide, and a minor amount of water (total of 100 mL) which had been prepared by air oxidation of alpha-methyl benzyl alcohol was then fed into the autoclave over a 15 minute period while constantly stirring the autoclave contents. During the addition, the reaction exothermed to 85° C. The reaction mixture was stirred an additional 30 minutes after addition was completed. After cooling in an ice bath, the contents of the autoclave were analyzed for hydrogen peroxide by iodometric titration and for propylene oxide by gas chromatography. The results obtained were as follows: Final $H_2O_2$ concentration=0.11% (0.0040 mole) $H_2O_2$ conversion=97% Propylene oxide produced=0.12 mole Selectivity to propylene oxide (based on hydrogen peroxide)=84%

Propylene oxide and catalyst are recovered from the reaction product as described in Step C of Example 1 and the resulting acetophenone/alpha-methyl benzyl alcohol mixture hydrogenated over a supported palladium catalyst to recycle substantially all of the acetophenone back to alpha-methyl benzyl alcohol.

EXAMPLES 6-7

These examples demonstrate that the integrated process of this invention, which uses a "crude" (unpurified) oxidant mixture obtained by air oxidation of an aryl-substituted secondary alcohol, provides epoxide yields equivalent to those obtained using purified hydrogen peroxide diluted in a "clean" alcohol/ketone reaction medium.

A 300 ml glass-lined autoclave equipped with a Teflon stir shaft and blade and thermowell was charged with methanol (25 ml) and "TS-1" titanium silicalite catalyst (0.73g), followed by liquid propylene (16 mL; 0.20 mole). The autoclave was heated to 37° C. by means of an external coil attached to a circulating bath. A crude oxidant mixture (100 mL) obtained by air oxidation of alpha-methyl benzyl alcohol and containing 5.15 weight percent hydrogen peroxide was charged to an Isco pump and added to the contents of the autoclave over a 1 hour period. The reaction mixture exothermed to 45° C. and was stirred at this temperature for an additional 2 hours after addition was completed. The pressure dropped from 120 psia to ca. 42 psia during the reaction. The external heating cord was replaced with an ice bath and the liquid contents of the autoclave cooled to 20° C. The autoclave was vented and the head removed for product sampling. The reaction product was analyzed by iodometric titration (residual hydrogen peroxide) and gas chromatography (organic products). The results are shown in Table I below (Example 6). Epoxide selectivity with respect to olefin was over 99%, with no detectable amount of propylene glycol and less than 1% of 2-methoxy-1-propanol and 1-methoxy-2-propanol being produced.

When the above procedure was repeated using an artificial oxidant mixture prepared by stirring reagent grade alpha-methyl benzyl alcohol (70 mL), acetophenone (30 mL), and 50% aqueous hydrogen peroxide (10 mL) with magnesium sulfate (30 g; used to remove all but ca. 1% water from mixture) and filtering, no significant difference in $H_2O_2$ conversion, epoxide selectivity, or epoxide yield was observed (Comparative Example 7).

TABLE I

| Example No. | % $H_2O_2$ Conversion | % PO Selectivity | % PO Yield |
|---|---|---|---|
| 6 | 87 | 88 | 77 |
| 7* | 90 | 87 | 78 |

*comparative example

EXAMPLES 8-9

Examples 6-7 were repeated at a reaction temperature of 80° C. instead of 45° C. The results obtained (Table II) confirmed that, contrary to expectation, no loss in epoxide selectivity or yield occurs when using an unpurified oxidant mixture prepared by air oxidation of an aryl-substituted secondary alcohol.

TABLE II

| Example No. | % $H_2O_2$ Conversion | % PO Selectivity | % PO Yield |
|---|---|---|---|
| 8 | 97 | 83 | 81 |
| 9* | 95 | 84 | 80 |

*comparative example (using purified reagent grade reactants)

EXAMPLES 10-11

A flask was charged with methanol (1.6 mL), "TS-1" titanium silicalite catalyst (0.13 g), allyl chloride (4.6 m mole), and an oxidate mixture containing 5.15 weight % hydrogen peroxide (1.9 m mole) prepared by air oxidation of alpha-methyl benzyl alcohol. The flask was fitted with a reflux condenser and submerged in a 40° C. oil bath for 3 hours. The reaction mixture thus obtained was analyzed for untreated hydrogen peroxide by iodometric titration and for organic products by gas chromatography (Example 10 of Table III). The yield of epichlorohydrin obtained was comparable to that observed using a highly purified oxidant mixture prepared by continuing reagent grade components (Comparative Example 11). This example also demonstrates that the process of the invention is useful for the production of halogenated epoxides.

TABLE III

| Example No. | % $H_2O_2$ Conversion | % Epoxide Selectivity | % Epoxide Yield |
|---|---|---|---|
| 10 | 64 | 88 | 56 |
| 11* | 58 | 90 | 52 |

*comparative example

COMPARATIVE EXAMPLE 12

This example demonstrates the criticality of selecting a titanium silicalite for use as an epoxidation catalyst in the process of the invention.

A 300 mL glass-lined autoclave equipped with a "Teflon" stir shaft and blade and thermowell was charged with methanol (25 mL) and a $TiO_2/SiO_2$ non-zeolitic supported catalyst prepared as described in U.S. Pat. No. 3,923,843 (0.56 g; 1.0% $TiO_2$ on silica). After sealing the autoclave, liquid propylene (16 mL; 0.20 mole) was added. The autoclave was heated to 37° C. using an external coil attached to a circulating bath. An attached Isco pump was charged with an oxidant mixture prepared by air oxidation of alpha-methyl benzyl alcohol (100 mL; 4.77% $H_2O_2$; 0.140 mole). The oxidant mixture was added over a 1 hour period; no exotherm was observed. After stirring for an additional 2 hours at 37° C., the external coil was replaced by an ice bath and the contents of the reaction cooled to 20° C. The autoclave was vented and the head removed. The reaction mixture was analyzed by iodometric titration for residual hydrogen peroxide and by gas chromatography for volatile organic products. Only 16% $H_2O_2$ conversion was observed; no propylene oxide was detected. This result confirms that high yields of epoxide cannot be obtained using this type of heterogeneous catalyst and an oxidant mixture comprising aryl-substituted secondary alcohol, aryl-substituted ketone, and hydrogen peroxide, even though the catalyst, like titanium silicalite, predominantly contains only titanium, oxygen, and silicon. Apparently, the arrangement of titanium and silicon atoms within a crystalline molecular sieve-type structure is crucial in order for such substances to function effectively as olefin epoxidation catalysts.

COMPARATIVE EXAMPLE 13

This example demonstrates the importance of using an oxidant mixture derived from air oxidation of an aryl-substituted secondary alcohol rather than an organic hydroperoxide as the source of active oxygen during the epoxidation step of the process of this invention.

A 300 mL autoclave equipped as described in Comparative Example 12 was charged with a 3.0 M solution of tert-butyl hydroperoxide in 2,2,4-trimethyl pentane (50 mL; 0.15 mole TBHP) and "TS-1" titanium silicalite catalyst (1.10 g). After adding liquid propylene (70 mL; 0.87 mole), the autoclave was heated and stirred at 45° C. for 3 hours. Only 12% t-butyl hydroperoxide conversion was observed. No detectable amount of propylene oxide was present, indicating that t-butyl hydroperoxide cannot be successfully substituted for an oxidant mixture derived from oxidation of an aryl-substituted secondary alcohol in the process of this invention.

EXAMPLE 14

The procedure of Example 10 is repeated using allyl alcohol as the olefin instead of allyl chloride and a reaction temperature of 25° C. The expected product is glycidol.

EXAMPLE 15

The procedure of Example 10 is repeated using trans-2-hexene a the olefin and a reaction temperature of 62° C. The expected product is 2,3-hexene oxide.

We claim:

1. An integrated process for the production of an epoxide comprising the steps of
   (a) contacting an aryl-substituted secondary alcohol with molecular oxygen under conditions effective to form an oxidant mixture comprised of the secondary alcohol, an aryl-substituted ketone, and hydrogen peroxide;
   (b) contacting the oxidant mixture with an olefin and a catalytically effective amount of a titanium silicalite for a time and at a temperature effective to convert the olefin to the epoxide; and
   (c) reacting the aryl-substituted ketone with hydrogen in the presence of a transition metal hydrogenation catalyst under conditions effective to convert the ketone to the aryl-substituted secondary alcohol.

2. The process of claim 1 wherein the titanium silicalite has an MFI or MEL topology.

3. The process of claim 1 wherein the titanium silicalite has a composition corresponding to the chemical formula $$xTiO_2 \cdot (1-x) SiO_2$$

wherein x is from 0.0001 to 0.125.

4. The process of claim 1 wherein the aryl-substituted secondary alcohol has the general structure:

wherein R and R$^1$ are the same or different and are selected from the group consisting of alkyl, aryl alkyl, and aryl groups with the proviso that at least one of R or R$^1$ is an aryl group.

5. The process of claim 1 wherein the aryl-substituted secondary alcohol has the general structure

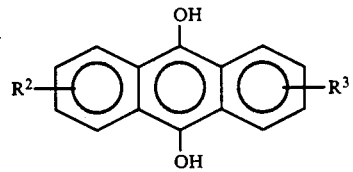

wherein R$^2$ and R$^3$ are the same or different and are selected from hydrogen and C$_1$-C$_{10}$ alkyl.

6. The process of claim 1 wherein the olefin has the general formula

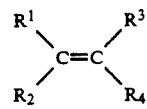

wherein R$^1$, R$^2$, R$^3$, and R$^4$ are the same or different and are selected from hydrogen, C$_1$-C$_{20}$ alkyl, C$_7$-C$_{20}$ aryl alkyl, C$_5$-C$_{12}$ cycloalkyl, C$_6$-C$_{20}$ alkyl cycloalkyl and C$_6$-C$_{20}$ aryl.

7. The process of claim 1 wherein the amount of titanium silicalite is from 0.01 to 10 grams per mole of olefin.

8. The process of claim 1 wherein step (b) in said process is conducted at a pressure of between 1 and 100 atmospheres.

9. The process of claim 1 wherein the molar ratio of Si:Ti in the lattice framework of the titanium silicalite is from 9.5:1 to 99:1.

10. The process of claim 1 wherein the molar ratio of olefin:hydrogen peroxide in step (b) is from 1.10 to 10:1.

11. The process of claim 1 wherein methanol is additionally present during step (b).

12. The process of claim 1 wherein the temperature in step (b) is from 0° C. to 150° C.

13. The process of claim 1 wherein the titanium silicalite has been treated with an acid-neutralizing agent selected from alkaline substances and silylating agents.

14. The process of claim 1 comprising the additional step of separating the epoxide from the aryl-substituted secondary alcohol and the aryl-substituted ketone prior to step (c).

15. The process of claim 1 wherein the transition metal in the transition metal hydrogenation catalyst in step (c) is selected from palladium, platinum, chromium, rhodium, nickel, or ruthenium.

16. The process of claim 1 wherein step (c) is carried out at a temperature of from 0° C. to 200° C.

17. The process of claim 1 wherein step (c) is conducted at a hydrogen pressure of between 1 and 200 atmospheres.

18. The process of claim 1 wherein step (a) is conducted at a temperature of from 100 to 200° C.

19. The process of claim 1 wherein step (a) is conducted at a pressure of from 50 to 1000 psig.

20. The process of claim 1 wherein the oxidant mixture contains less than 4 weight percent water.

21. The process of claim 1 wherein contacting step (a) is carried out in a liquid phase.

22. An integrated process for the production of an epoxide comprising the steps of
   (a) contacting alpha-methyl benzyl alcohol with molecular oxygen at a temperature of from 100° C. to 200° C. and a pressure of from 50 to 1000 psig oxygen to form an oxidant mixture comprised of alpha-methyl benzyl alcohol, acetophenone, and from 1 to 10 weight percent hydrogen peroxide;
   (b) contacting the oxidant mixture with an olefin and from 0.01 to 10 grams titanium silicalite per mole of olefin having an MEL or MFI topology and a chemical formula $$xTiO_2 \cdot (1-x)SiO_2$$

wherein x is from 0.01 to 0.125, at a temperature of from 0° C. to 150° C. for a time effective to convert the olefin to epoxide; and
   (c) reacting the acetophenone with hydrogen in the presence of a transition metal hydrogenation catalyst wherein the transition metal is platinum, palladium, chromium, rhodium, nickel or ruthenium at a temperature of from 20° to 150° C. and a hydrogen pressure of from 1 to 200 atmospheres to convert the acetophenone to alpha-methyl benzyl alcohol.

23. The process of claim 22 wherein the olefin is selected from ethylene, propylene, 1-butene, isobutylene, 2-butene, 1-pentene, cyclohexene, allyl chloride, allyl alcohol, and butadiene.

24. The process of claim 22 wherein the oxidant mixture contains less than 4 weight percent water.

25. The process of claim 22 wherein contacting step (a) is carried out in a liquid phase.

26. The process of claim 22 wherein the Si:Ti molar ratio in the lattice framework of the titanium silicalite is from 9.5:1 to 60:1.

27. The process of claim 22 comprising the additional step of separating the epoxide from the aryl-substituted secondary alcohol and the aryl-substituted ketone by distillation prior to step (c).

28. The process of claim 22 wherein the titanium silicalite has been treated with an acid-neutralizing agent selected from alkaline substances and silylating agents.

* * * * *